US008892193B2

(12) United States Patent
Moulder et al.

(10) Patent No.: US 8,892,193 B2
(45) Date of Patent: Nov. 18, 2014

(54) APPARATUS AND METHOD FOR DETECTION OF LEAD FAILURE IN AN IMPLANTABLE MEDICAL DEVICE (75) Inventors: J. Christopher Moulder, Portland, OR (US); Jie Lian, Beaverton, OR (US)

(73) Assignee: Biotronik SE & Co. KG (DE)

( * ) Notice: Subject to any disclaimer, the term of this patent is extended or adjusted under 35 U.S.C. 154(b) by 241 days.

(21) Appl. No.: 13/329,363

(22) Filed: Dec. 19, 2011

(65) Prior Publication Data
US 2012/0179056 A1 Jul. 12, 2012

Related U.S. Application Data (60) Provisional application No. 61/431,862, filed on Jan. 12, 2011.

(51) Int. Cl.
*A61B 5/0452* (2006.01)
*A61N 1/37* (2006.01)
(52) U.S. Cl.
CPC ............... *A61N 1/3704* (2013.01); *A61N 1/37* (2013.01)
USPC .............................................. 600/509; 607/2
(58) Field of Classification Search
USPC .............................................. 600/509; 607/2
See application file for complete search history.

(56) References Cited

U.S. PATENT DOCUMENTS

| 6,862,476 | B2 | 3/2005 | Mouchawar et al. |
| 7,603,172 | B2 | 10/2009 | Lian et al. |
| 7,747,320 | B1 | 6/2010 | Kroll et al. |
| 8,060,198 | B2 | 11/2011 | Lian et al. |
| 2007/0276447 | A1* | 11/2007 | Sanghera et al. ............... 607/32 |
| 2008/0275517 | A1 | 11/2008 | Ghanem et al. |
| 2009/0187227 | A1 | 7/2009 | Palreddy et al. |
| 2010/0106209 | A1 | 4/2010 | Gunderson et al. |
| 2012/0071944 | A1 | 3/2012 | Gunderson et al. |

OTHER PUBLICATIONS

Brignole et al., "Improved Arrhythmia Detection in Implantable Loop Recorders", *Journal of Cardiovascular Electrophysiology*, 19: 928-934, 2008.
European Search Report, Application No. 11193752.0-2305, Apr. 4, 2012.

* cited by examiner

*Primary Examiner* — Alyssa M Alter
(74) *Attorney, Agent, or Firm* — Craig A. Fieschko, Esq.; DeWitt Ross & Stevens S.C.

(57) ABSTRACT

A method for automatic threshold control and detection of lead failure in an implanted medical device obtains three sensing vectors for measurement of an electrocardiogram signal. A dynamic error signal is determined from the vectors, and may be used to set a detection threshold for insufficient ECG signals, and/or to passively monitor the device for indications of lead failure without performing an impedance measurement. Passive mode operation conserves battery power and enables continuous lead integrity checks. A quality factor may also be determined from the error signal, to indicate whether or not signal measurements are valid with respect to noise levels. If the detection threshold is allowed to decay between successive features of the electrocardiogram, the decay rate may be made adaptive such that it automatically adjusts to changes in heart rate or to changes in amplitude of the electrocardiogram features.

23 Claims, 6 Drawing Sheets

APPARATUS AND METHOD FOR DETECTION OF LEAD FAILURE IN AN IMPLANTABLE MEDICAL DEVICE

CROSS-REFERENCE TO RELATED APPLICATIONS

This patent application claims the benefit of U.S. Provisional Patent Application No. 61/431,862, filed on Jan. 12, 2011, which is hereby incorporated by reference in its entirety.

FIELD OF THE INVENTION

The invention relates to detection of faulty leads in implantable medical devices (IMDs), and/or to reduction of noise and false signals in implantable medical devices (IMDs).

BACKGROUND OF THE INVENTION

Figure 1:
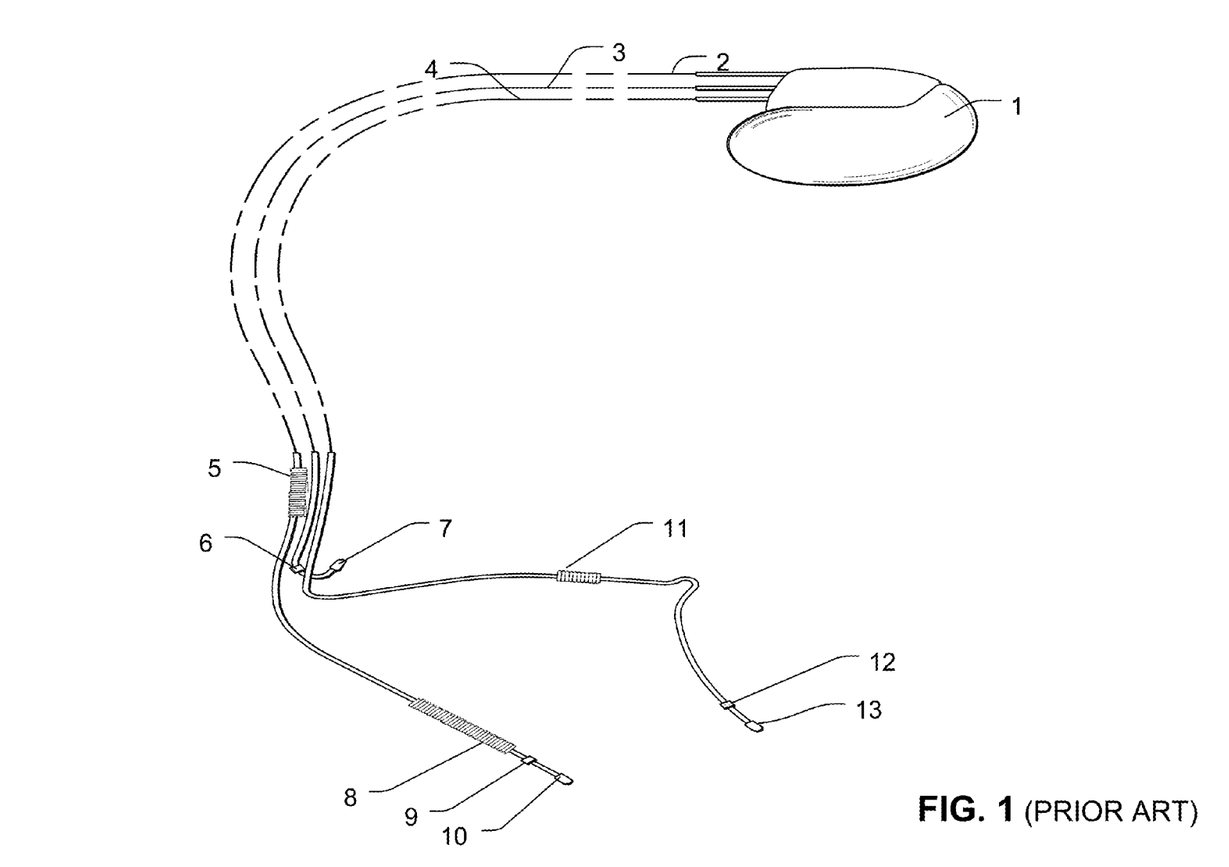
FIG. 1 is a perspective view of an exemplary prior art implantable medical device (IMD) having three leads, with nine different electrodes placed along the leads.

As shown in FIG. 1, implantable medical devices (IMDs) 1, including implantable pulse generators (IPGs), implantable cardioverter-defibrillators (ICDs), implantable loop recorders (ILRs), and other subcutaneous implantable devices, use leads, e.g., insulated wires 2-4, inserted through the vasculature to the heart to provide therapy via electrodes 5-13 placed along, or at the ends of, the leads 2-4. As shown, electrodes 7, 10, and 13 are tip electrodes, electrodes 6, 9, and 12 are ring electrodes, and electrodes 5, 8, and 11 are defibrillation electrodes. Lead failures have become one of the most common modes of hardware failure in IMD systems. Statistics show that, for example, five years after implantation of a device, the failure rate for ICD leads is 15%, and that eight years after implantation, the lead failure rate increases to 40%. Causes of lead failure may include, for example, insulation breach, lead fracture, and loose set screws. Partial failure of the electrical insulation of an ICD is particularly troublesome, and may result when the lead rubs against the ICD housing, thereby thinning the insulation and potentially short-circuiting high voltage components. Meanwhile, low voltage impedance checks for detecting insulation failure can remain unaffected. Lead rubbing eventually causes lead fracture, which may have significant detrimental consequences for a cardiac patient, including inhibited pacing, inappropriate shocks, pacing capture failure, premature battery depletion, or failure to defibrillate when needed.

A conventional method of detecting lead failure entails performing a low voltage impedance check by delivering a small shock through a lead in the form of a low amplitude waveform, and then measuring the impedance. If the measured impedance is outside a prescribed "normal" range, lead failure is indicated. A second method is to check for the presence and frequency of ultra-short non-physiological sensing intervals.

The impedance measurement method of detecting lead failure has proven to be inadequate. Impedance monitoring does not reliably detect early lead malfunction, and it has been reported that impedance monitoring has failed to prevent inappropriate shocks in two thirds of patients studied. Impedance monitoring also requires specialized circuitry to source low-current pulses and measure the resulting impedance. This circuitry must also enable the IMD to deliver a therapeutic shock while substantially simultaneously making voltage and current measurements to determine the impedance. Other methods of detecting lead failure, as mentioned above, are more effective but still have difficulty in differentiating artifacts associated with lead failure from exogenous noise that may originate from other sources such as muscle activity.

Another class of IMD, for example implantable loop recorders (ILRs), does not use leads to sense cardiac activity. Instead, ILRs detect far-field cardiac signals present in a subcutaneous ECG (SECG) signal. (The term ECG as used hereinafter may refer to electrocardiograms, subcutaneous electrocardiograms, or intracardiac electrograms.) Thus, in addition to detecting lead failure, achieving optimum performance of an IMD requires the ability to recognize noise in an SECG or in other lead signals. In particular, it is desirable to recognize a central feature of interest within an ECG signal, known to those skilled in the art as a "QRS complex." Near-field noise is capable of corrupting ECG signals in IMDs, and may cause over- or under-detection of cardiac arrhythmias. Although detection of noise is critical to device performance, existing solutions to account for noise in an implantable loop recorder are inadequate. To prevent noise, implantable cardiac devices may be placed at a location where the heart signal is maximized, but this imposes an additional burden on the physician. It is also known that noise may be reduced through the use of standard filtering techniques or by manually adjusting sensing parameters. However, existing devices sense the ECG using only a single pair of electrodes, i.e., using a single signal vector or channel. Brignole et al., *Journal of Cardiovascular Electrophysiology*, 19: 928-934, 2008, describe a sensing method for use in an ILR in which sensing thresholds for ECG signals are adapted to the peak of the R-wave within the QRS complex, and the threshold decreases to a minimum value. Although this method is new for ILRs, it is common practice in other devices such as IPGs and ICDs. Furthermore, although both high frequencies and amplifier saturation are sensed to further reduce false signal detection, relying on a single channel and only adapting it to the peak of the R-wave are insufficient. Even if noise is correctly detected, the ILR is susceptible to remaining in noise mode if the minimum threshold is set too low. Conversely, the ILR is susceptible to under-sensing if the minimum threshold is set too high. Often, the minimum threshold is fixed by the physician at the time of implantation of the device and cannot be changed. Methods that rely on these fixed QRS sensing thresholds, or even methods such as that presented in U.S. Patent Application Publication No. 2009/0187227A1 (which discloses the use of dynamic detection thresholds), can incur significant risk depending on the basis for changing those thresholds. Furthermore, arrhythmia classifications that are based on QRS detection are at increased risk for being incorrect if noise is mistaken for a true signal. Finally, another drawback of these methods is that they do not sense general signal quality, nor do they detect whether or not the signal to noise ratio is high enough to reliably differentiate noise from the signal itself.

What is needed is a method of reducing noise-induced false QRS signal detection, along with an improved method of detecting faulty leads.

SUMMARY OF THE INVENTION

A method is disclosed for automatic threshold control and detection of lead failure in an implanted medical device (LIVID), and for analyzing a far-field electrogram based on evaluation of its baseline peak-to-peak amplitude. A preferred version of the method entails providing at least three sensing electrodes for measurement of an electrocardiogram signal via at least three input vectors, determining a dynamic error signal from the three input vectors, and computing a dynamic detection threshold value from the error signal such that the detection threshold automatically adjusts to changes in the error signal. A low signal flag may also be determined from the dynamic threshold. Furthermore, a quality factor may also be determined from the error signal, with the quality factor indicating whether or not the input signals are valid. It may be decided to suspend further sensing if an input signal is found to be invalid. If the dynamic detection threshold is allowed to decay between successive features of the electrocardiogram, the decay rate may be made adaptive such that it automatically adjusts to changes in heart rate or to changes in amplitude of the features of the electrocardiogram. The same dynamic error signal that is used in computing the dynamic detection threshold may be used to passively detect lead failure associated with an implanted medical device (IMD), without performing an impedance measurement. Performing multiple three-vector comparisons can further pinpoint the source of the lead failure.

The use of dynamic detection thresholds for lead failure detection and noise detection, where the thresholds are based on an error signal, provides several advantages. One advantage of the preferred method is that it operates continuously and passively. No current injection circuits are required for implementation. There also is no requirement to initiate a test to determine lead failure, for example. Instead, the error is simply monitored passively until a failure is detected. Passive mode operation, instead of active mode operation, can timely detect lead failure at its onset, and conserve battery power in the implanted device.

DETAILED DESCRIPTION OF PREFERRED VERSIONS OF THE INVENTION

Versions of the invention will be readily understood from the following detailed description in conjunction with the accompanying drawings, wherein like reference numerals designate like structural elements. The accompanying drawings illustrate exemplary versions of the invention, and the invention is not limited to these drawings.

Detection of both lead failure and noise may be addressed by a preferred method that uses error detection on multiple sensing channels. Instead of using only one pair of sensing electrodes, at least three sensing electrodes, and thus at least three sensing vectors, may be used to detect noise in a cardiac signal. In order to accomplish this, the IMD hardware is preferably configured with an electronic switch circuit that can select at least three sensing channels for substantially simultaneous measurement of an intracardiac electrogram.

Figure 2:
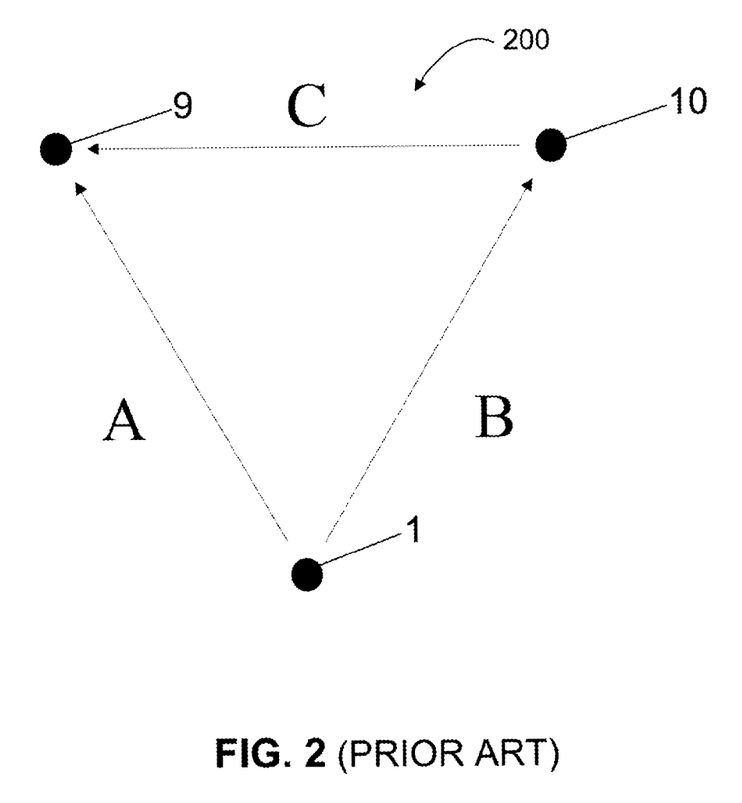
FIG. 2 is a prior art triangular vector map that shows the relationship between three sensing vectors associated with three of the electrodes shown in FIG. 1.

Referring to FIG. 2, input signals in the form of sensing vectors A, B, and C are shown arranged in a triangular vector map 200. The dots shown in FIG. 2 represent three of the electrodes shown in FIG. 1, such as a ring electrode 9 and a tip electrode 10 along lead 2, and the IMD housing (or "can") 1. Whereas previous methods have used a three-terminal measurement ("half-cell potential"), in which the terminals are physically different, using the present method, the leads and electrodes may be structurally identical i.e., made of the same materials, differing only in their placement. Vector A represents a potential difference between the two points at which electrodes 9 and 1 are located; vector B represents a potential difference between the two points at which electrodes 10 and 1 are located; and vector C represents a potential difference between the two points at which electrodes 9 and 10 are located. The input signals A, B, and C will be shown below to dynamically determine three important noise detection parameters.

Theoretically, in the configuration shown, A−B−C=0, i.e., the voltage measurement for vector A should equal the sum of the two voltage measurements for vectors B and C. However, in practice, A−B−C yields an error signal epsilon ($\epsilon$) that includes two components. A first error signal component is associated with inherent system noise introduced by local electronics such that, on average, the inherent system noise does not change. A second error signal component changes over time according to external, "far-is field" conditions such as, but not limited to, a) uncorrelated noise present on the electrodes, b) muscle potentials, or c) electrode rubbing. This extraneous noise includes, for example, myopotential noise generated by muscles in the vicinity of the heart or IMD such as pectoral muscle, inter-costal muscles, or diaphragm muscle. The extraneous noise is projected to all of the sensing vectors A, B, and C. According to vector arithmetic, the contribution to the error signal epsilon ($\epsilon$) by the extraneous noise should cancel out so that epsilon ($\epsilon$) is essentially characterized by the first component associated with local electrical activity internal to each channel.

However, in the event of an individual lead wire fracture, artifacts due to lead failure are only present in the sensing vector involving the failed lead, so these artifacts are not cancelled out when computing the error signal epsilon ($\epsilon$). Instead, a large difference becomes evident in the measurement obtained by two alternate paths: A vs B+C, which manifests itself as a spike in the error signal epsilon ($\epsilon$). A typical increase indicating failure of a single conductor raises the value of epsilon ($\epsilon$) by a factor of at least 2. If there is a sudden rise or a sustained rise in the maximum value of epsilon ($\epsilon_{max}$), the presence of noise is established and subsequently, a lead failure is predicted. Other metrics characterizing the noise level (e.g., threshold crossing count or standard deviation of the sample amplitude histogram) can also be used to detect an increase in the noise level.

Thus, continuous passive monitoring of the error signal epsilon ($\epsilon$) (or periodic calculation, e.g., on every heartbeat) is useful as an indicator of lead failure, although it may not indicate which lead has failed unless multiple three-vector comparisons are performed. For example, in the illustrated case it is not known which conductor failed within lead 2, the one supplying electrode 9 or the one supplying electrode 10. To discern which conducting wire is broken, more vectors must be employed, such as would be available if multiple leads were implanted (e.g., both leads 2 and 3 shown in FIG. 1). For example, if vectors formed by electrodes 6, 7, and 1 show a very small error signal, this would indicate that lead 3 is functioning properly. Therefore, if vectors formed by electrodes 6, 7, and 9 show a large error signal, it can be deduced that the conductor between electrodes 9 and 1 has failed. On the other hand, if vectors formed by electrodes 6, 7, and 10 show a large error signal, one can deduce that the conductor between electrodes 10 and 1 has failed.

The error signal epsilon ($\epsilon$) may also be used to determine a dynamically changing minimum sensing threshold, instead of using a fixed minimum sensing threshold. The changing minimum sensing threshold may then be used to determine when a sensed signal has too low an amplitude to reliably produce accurate beat detections in the presence of noise.

According to a preferred method of noise detection, a minimum detection threshold may be set within limits defined by a "lowest absolute threshold" (LAT), and a "low signal flag (LSF)" may then be calculated from the LAT when the peak signal is not sufficiently large.

In the preferred method, LAT and LSF are calculated according to equations $$\text{LAT} = k|\epsilon_{max}|, \text{ and} \quad (1)$$

$$\text{LSF} \propto \text{QRS}_{peak}/\text{LAT}, \quad (2)$$

respectively, wherein k is a constant multiplier, typically having a value between 1 and 4, that is used to adjust the amplitude of LAT based on preconditioning of the input signals, e.g., if the input signals are additively combined, spatially or temporally, then k=3. LAT and LSF are thus dynamic quantities because they depend directly on an error signal that is constantly changing.

Referring to equation (1), $\epsilon_{max}$ is the maximum of the error within a predetermined time interval, which may depend on cycle length or detections, or which may be set to a prescribed value such as 1 second. LAT is the lowest value that can be assigned to the detection threshold such that if the detection threshold falls below LAT, it is reset to LAT. It is noted that LAT, being proportional to a maximum value of the error signal epsilon ($\epsilon$), and therefore being derived from the three input signals A, B, and C, is therefore also a dynamic quantity that automatically adjusts to changes in the noise level. LAT may be thought of as the level below which there is noise, and above which there is a true cardiac signal. Thus, as the maximum strength of the inherent system noise increases, the minimum signal threshold increases as well to ensure that the noise is not mistaken for a true QRS event. During periods of low noise amplitude and low signal amplitude, the LAT is may be decreased in order to ensure that the low amplitude signal can be detected. In this way, dynamically setting LAT avoids both oversensing of noise and undersensing of low amplitude signals. This is not possible with a fixed sensing threshold.

Referring to equation (2), LSF may be calculated so that if the peak of the detected signal is less than a predefined multiple (e.g., 2) of the LAT, a low signal is declared. Thus, if the noise level decreases, the peak amplitude of a valid sensed signal may also decrease without being mistaken for noise. LSF may therefore be thought of as a noise threshold. LSF may be channel specific such that there exists an LSF for each channel.

Figure 3:
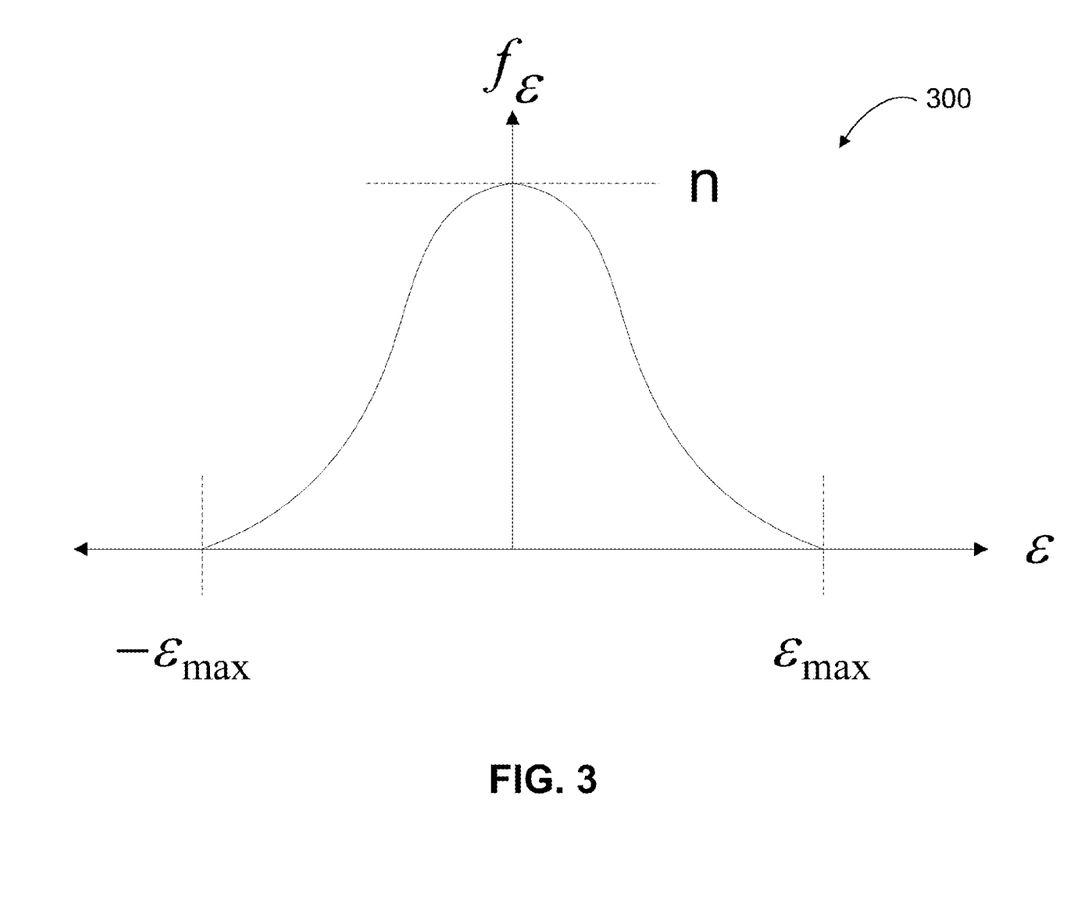
FIG. 3 is a plot of a Gaussian-distributed error signal $f(\epsilon)$.
Figure 4:
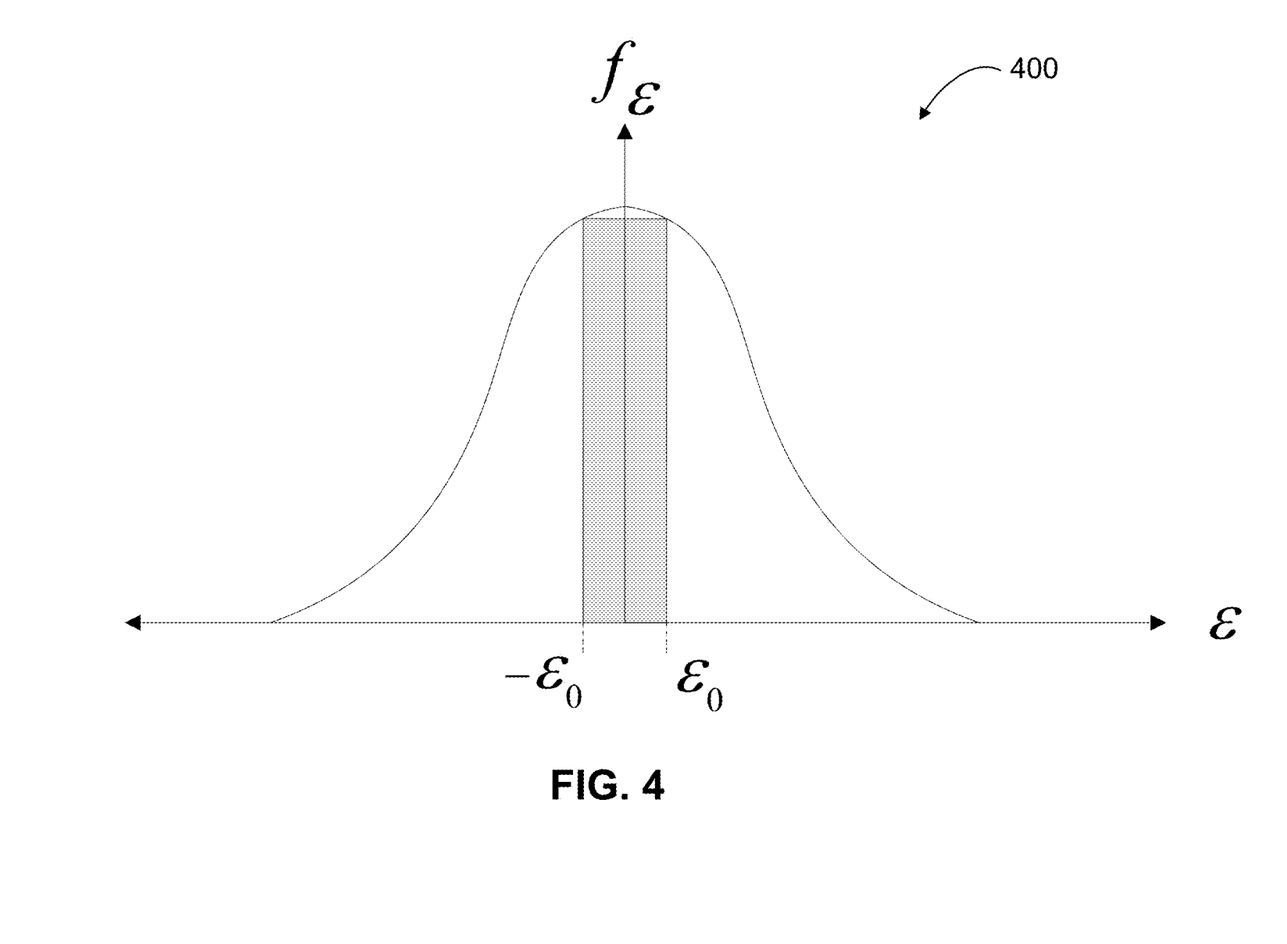
FIG. 4 is a plot of a Gaussian-distributed error signal $f(\epsilon)$ indicating how a histogram may be derived from the distribution.

Referring to FIG. 3, a Gaussian distribution plot 300 may be used to assess signal quality. Plot 300 is a graph of a distribution function f($\epsilon$) that represents a collection of n error signal measurements that fall between the values $-\epsilon_{max}$ and $\epsilon_{max}$. If f(s) has a narrower, taller shape, distribution plot 300 indicates better quality sensed signals than if f(s) has a wider, shorter shape. With reference to FIG. 4, a histogram 400 may be formed by sectioning f(s) along the $\epsilon$ axis into bins of a certain width, and counting up the number of samples in each bin. Thus, the number of samples that fall within the range of $-\epsilon_o$ to $+\epsilon_o$ are counted to provide an indication of the height of the distribution. The signal quality Q may be given by the equation $$Q = n_{\epsilon o}/(\kappa \epsilon_{max}), \quad (3)$$

wherein $\kappa$ is a constant having a default value of 2, and $\epsilon_o$ is chosen to be a number smaller than $\epsilon_{max}$. For example, if the inherent system noise is about +/−20 µV, $\epsilon_o$ may be chosen as 10 µV.

The quality factor Q is therefore a statistical measure that represents the shape of the error distribution function f($\epsilon$). As the amplitude of the noise increases, $\epsilon_{max}$ increases, n decreases, and Q decreases, indicating that the signal quality is becoming degraded. This degradation in quality may indicate early lead failure that would otherwise go undetected. Q is preferably normalized to its peak amplitude, $Q_{max}$, so that the values of Q fall between 0 and 1 allowing a direct comparison to be made at different times. Then, if the normalized value of Q falls below, for example, 25% or 0.25, the IMD system can react by suspending further sensing, because it is unlikely that valid signals can be determined when the quality factor is so low.

A decay time of the dynamic detection threshold may also be dynamically changed based on an average QRS cycle length, in which the cycle length may be defined as the time interval between successive QRS peaks. The average cycle length may be accumulated by calculating an initial average and then updating it whenever a known good sensed event is recognized by the system. Furthermore, changing the time period during which the minimum sensing threshold is reduced tends to increase detection accuracy, while reducing the possibility of detecting noise or T-waves (features of an ECG signal that appear after the QRS complex).

Figure 5:
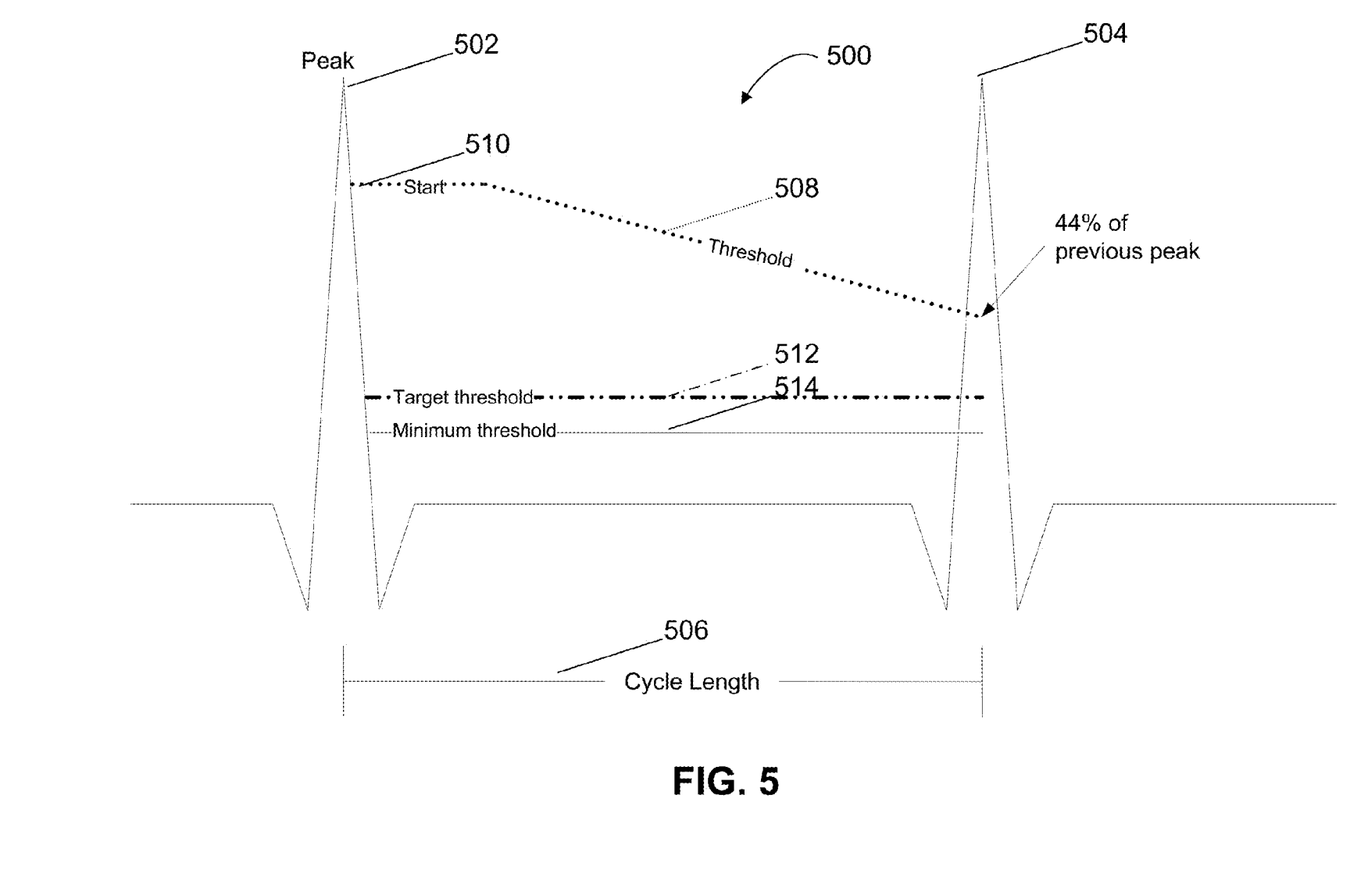
FIG. 5 is a plot depicting an exemplary adaptive detection threshold decay rate feature for varying a detection threshold between successive QRS signals.

Referring to FIG. 5, a graph of an ECG signal 500 as a function of time is shown, in which signal 500 exhibits a first QRS peak 502 and a second QRS peak 504, representing two successive heartbeats. A ventricular cycle length 506 is defined as the time interval between successive QRS peaks 502 and 504, i.e., the time interval between successive heart beats. As the heart beats faster, cycle length 506 becomes commensurately shorter. In state of the art devices, a dynamic detection threshold 508 is initialized at an initial value 510 equal to a prescribed fraction of first QRS peak 502, for example, 75%. Dynamic detection threshold 508 then decays in steps until it reaches a target threshold 512, for example, 25% of first QRS peak 502. An absolute minimum threshold (LAT) 514 is also maintained, below which the decaying detection threshold 508 cannot fall. If the rate of decay is too slow, undersensing may occur, and if the rate of decay is too rapid, oversensing may occur.

The present method proposes an improved dynamic detection threshold 508 in which automatic adjustment of the threshold decay rate occurs based on a moving average of ventricular cycle length 506. This method maintains the threshold 508 above the noise level, while allowing it to decay fast enough to detect the next expected heartbeat. The threshold decay adapts to changes in heart rate and to changes in QRS amplitude. According to a preferred version, the step duration of the threshold decay is adjusted so that the improved dynamic detection threshold 508 reaches target threshold 512 at a time is equal to the average cycle length 506. Therefore, despite changes in the heart rate, the dynamic threshold 508 reaches the target threshold 512 at a time coincident with the arrival of QRS peak 504. In the case of an ILR, as exemplified in FIG. 5, the dynamic detection threshold 508 may reach 44% of first QRS peak 502 at a time equal to the average cycle length 506.

Figure 6:
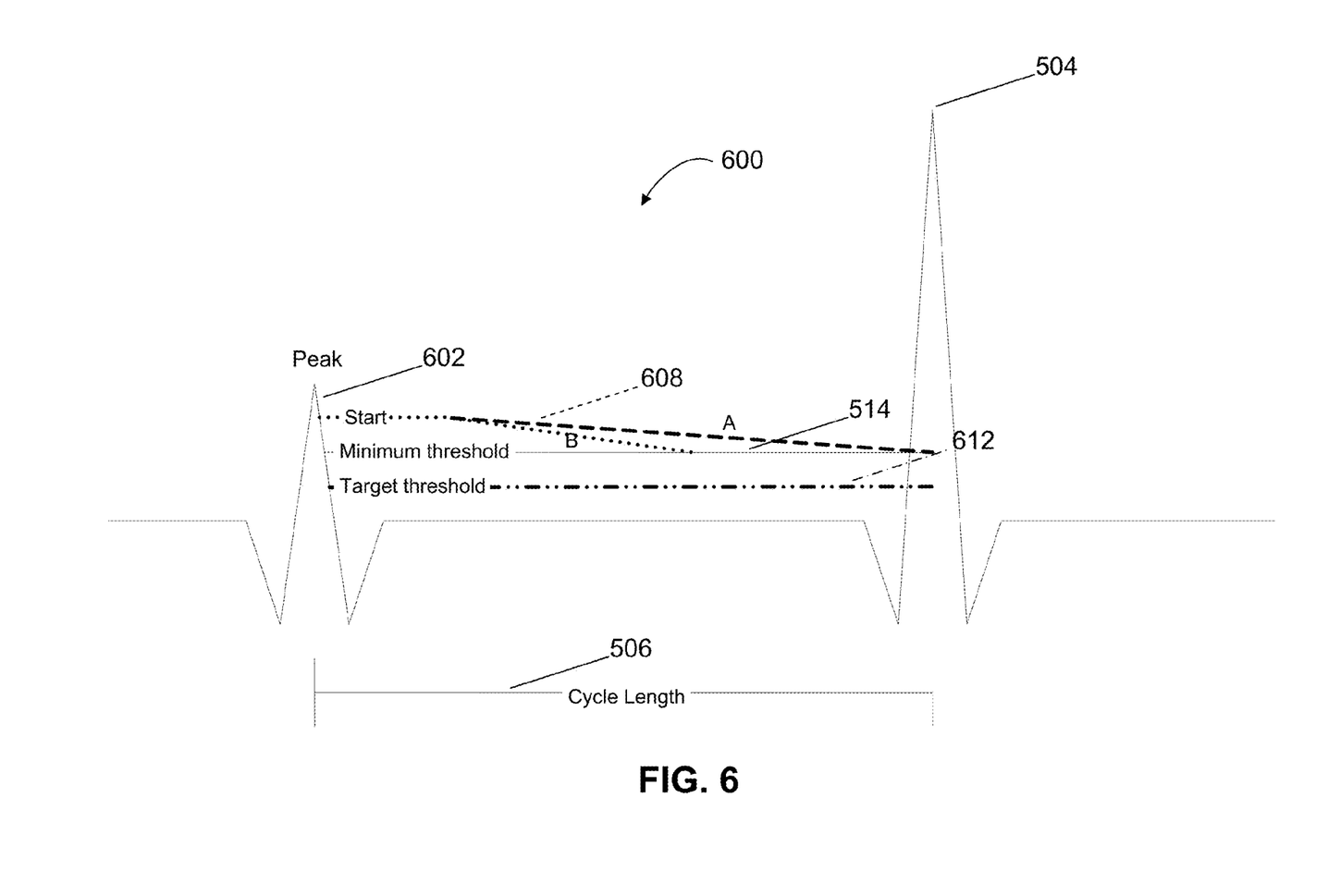
FIG. 6 is a plot illustrating the use of the adaptive detection threshold decay rate feature shown in FIG. 5, applied to a specific case in which there is a low initial peak amplitude.

Referring to FIG. 6, a special case 600 is depicted in which there exists a small peak QRS amplitude 602. In this case, the calculated target threshold 612 may be less than the minimum threshold 514. Because the detection threshold 608 may not fall below minimum threshold 514, detection threshold 608 would only decrease until it reached minimum threshold 514. So as to prevent the minimum threshold 514 from being reached too early (as illustrated by line B), according to a preferred version of the improved method, the time per decay step is adjusted (in this case, lengthened), and the number of decay steps is decreased, so that the minimum threshold 514 is reached coincident with the second QRS peak 504 (as illustrated by line A). Allowing for a dynamic decay step time maintains the dynamic threshold 606 above possible noise that may be present between QRS complexes, due to a T-wave, muscle noise, and the like.

Although certain versions have been illustrated and described herein, it will be appreciated by those of ordinary skill in the art that a wide variety of alternative or equivalent versions or implementations, intended to achieve the same purposes, may be substituted for the versions illustrated and described without departing from the scope of the present invention. Those skilled in the art will readily appreciate that versions in accordance with the present invention may be implemented in a very wide variety of ways. This application is intended to cover any adaptations or variations of the versions discussed herein.

The terms and expressions which have been employed in the foregoing specification are used therein as terms of description and not of limitation, and there is no intention, in the use of such terms and expressions, to exclude equivalents of the features shown and described or portions thereof, it being recognized that the scope of the invention is defined and limited only by the claims that follow.

It will be apparent to those skilled in the art that numerous modifications and variations of the described examples and versions are possible in light of the above teaching. The disclosed examples and versions are presented for purposes of illustration only. Therefore, it is the intent to cover all such modifications and alternate versions as may come within the true scope of this invention.

The invention claimed is:

1. A method of determining electrocardiogram (ECG) signal quality in an implantable medical device (IMD), the method including the steps of:
   a. sensing at least three ECG signals from at least three spaced electrodes;
   b. calculating at least three sensing vectors from the ECG signals, each vector representing the difference between ECG signals from a pair of the spaced electrodes, wherein each vector is obtained from a different one of the pairs of electrodes;
   c. calculating a dynamic error signal from the vectors, the dynamic error signal being dependent on the difference between:
      (1) one of the vectors, and
      (2) the sum of the other vectors; and
   d. adapting the sensing of the ECG signals in dependence on the dynamic error signal.

2. The method of claim 1 wherein at least two of the electrodes are connected to a casing via one or more leads.

3. The method of claim 1 wherein the dynamic error signal is calculated from three of the vectors.

4. The method of claim 1 further including the step of monitoring for an increase in the dynamic error signal indicative of failure of a lead extending to one of the electrodes.

5. The method of claim 1 wherein the sensing of the ECG signals is adapted if the dynamic error signal increases by a factor of approximately two or more.

6. The method of claim 1 further including the step of:
   a. for different sets of three electrodes, calculating three sensing vectors from each set;
   b. determining from the vectors whether one of the electrodes is experiencing failure in a lead extending to the electrode.

7. The method of claim 1 further including the step of
   a. for different sets of three electrodes, calculating three sensing vectors from each set;
   b. determining a dynamic error signal from each set of three vectors;
   c. monitoring each dynamic error signal for an increase indicative of failure of a lead extending to one of the electrodes.

8. The method of claim 1 further including the step of computing a dynamic detection threshold value from the dynamic error signal wherein:
   a. the dynamic detection threshold value is set above a noise level and below an ECG signal level, and
   b. the dynamic detection threshold value automatically adjusts to changes in the dynamic error signal.

9. The method of claim 1 further including the step of determining whether or not the ECG signals have sufficient amplitude in comparison to the dynamic detection threshold value to be considered valid.

10. The method of claim 9 further including the step of suspending further sensing of ECG signals if an ECG signal is determined to be invalid.

11. The method of claim 9, wherein the step of determining whether or not the ECG signals have sufficient amplitude includes:
   a. defining a low signal flag (LSF) indicative of insufficient ECG signal amplitude, and
   b. comparing at least one of the ECG signals to the LSF.

12. The method of claim 11, wherein the LSF varies in response to the dynamic error signal.

13. The method of claim 1 further including the step of determining a quality factor from the dynamic error signal, wherein the quality factor is indicative of whether the ECG signals are valid.

14. The method of claim 1 further including the step of decaying the dynamic detection threshold value between successive QRS complexes within the ECG signal, wherein the rate of decay varies with changes in the time between successive QRS complexes.

15. The method of claim 1 further including the step of decaying the dynamic detection threshold value between successive QRS complexes within the ECG signal, wherein the rate of decay varies with changes in the amplitude of a feature within the QRS complexes.

16. The method of claim 1 further including the step of computing a minimum detection threshold, wherein:
   a. no QRS peak is detected within an ECG signal if the ECG signal does not exceed the minimum detection threshold, and
   b. the minimum detection threshold is proportional to the dynamic error signal.

17. The method of claim 16 further including the step of computing a low signal flag, wherein:
   a. a low signal flag below a predefined limit is indicative of low signal quality within an ECG signal, and
   b. the low signal flag is proportional to the ratio of:
      (1) a peak value within the ECG signal, and
      (2) the minimum detection threshold.

18. The method of claim 1 further including the step of computing a dynamic detection threshold value, wherein:
   a. a subsequent QRS peak is detected within an ECG signal when the ECG signal exceeds the dynamic detection threshold value, and
   b. the dynamic detection threshold value dynamically decays from:
      (1) a maximum detection threshold proportional to a predefined fraction of a preceding QRS peak, to
      (2) a minimum detection threshold proportional to the dynamic error signal.

19. An implantable medical device (IMD) including:
   A. a casing, and
   B. at least three spaced electrodes, wherein at least two of the electrodes are connected to the casing via one or more leads,
   the IMD being configured to:
   a. sense at least three ECG signals from the electrodes;
   b. calculate at least three sensing vectors from the ECG signals, each vector representing the difference between ECG signals from a pair of the spaced electrodes, wherein:
      (1) each vector is obtained from a different one of the pairs of electrodes, and
      (2) the vectors collectively correspond to a closed path defined about the electrodes;
   c. calculate a dynamic error signal from the vectors, the dynamic error signal being dependent on the difference between:
      (1) one of the vectors, and
      (2) the sum of the other vectors; and
   d. adapt the sensing of the ECG signals in dependence on the dynamic error signal.

20. A method of determining electrocardiogram (ECG) signal quality in an implantable medical device (IMD), the IMD having three or more spaced electrodes, at least two of the electrodes being connected to a casing via one or more leads, each lead having one or more conductors therein, wherein the method includes the steps of:
   a. detecting ECG signals at each of at least three spaced electrodes;
   b. calculating at least three sensing vectors from three different pairs of the electrodes, wherein each vector represents the potential difference between ECG signals sensed at the electrodes within the vector's electrode pair;
   c. calculating a dynamic error signal representing a difference in potentials between vectors corresponding to electrodes arrayed about a closed path; and
   d. varying the detection of the ECG signals in dependence on the dynamic error signal.

21. The method of claim 20 further including the step of:
   a. computing a dynamic detection threshold value from the dynamic error signal;
   b. comparing the ECG signals to the dynamic detection threshold value; and
   c. varying the detection of the ECG signals if one or more of the ECG signals has an insufficiently low amplitude in comparison to the dynamic detection threshold value.

22. The method of claim 20 wherein the detection of the ECG signals is varied when an increase is detected in the dynamic error signal.

23. The method of claim 20:
   a. wherein four or more sensing vectors are calculated from different pairs of the electrodes, and
   b. further including the step of comparing different subsets of the sensing vectors to isolate one or more defective conductors.

* * * * *